United States Patent [19]

Berthold et al.

[11] 4,405,813

[45] Sep. 20, 1983

[54] PROCESS FOR THE PREPARATION OF 3,5-DIMETHYLANILINE

[75] Inventors: Rüdiger Berthold, Bad Soden am Taunus; Werner H. Müller, Eppstein, both of Fed. Rep. of Germany

[73] Assignee: Hoechst Aktiengesellschaft, Frankfurt am Main, Fed. Rep. of Germany

[21] Appl. No.: 318,116

[22] Filed: Nov. 4, 1981

[30] Foreign Application Priority Data

Nov. 6, 1980 [DE] Fed. Rep. of Germany ....... 3041899

[51] Int. Cl.$^3$ ...................... C07C 85/00; C07C 85/20
[52] U.S. Cl. ................................................. 564/415
[58] Field of Search ........................................ 564/415

[56] References Cited

U.S. PATENT DOCUMENTS 3,255,248  6/1966  Suessenguth et al. .......... 564/415 X
4,247,479  1/1981  Berthold ...................... 564/415 UX

FOREIGN PATENT DOCUMENTS 2623174  12/1977  Fed. Rep. of Germany ...... 564/415

OTHER PUBLICATIONS

"J. Amer. Chem. Soc.", 69, pp. 1907–1908, 1947.

Primary Examiner—Paul F. Shaver
Attorney, Agent, or Firm—Curtis, Morris & Safford

[57] ABSTRACT

Preparation of 3,5-dimethylaniline from 3,5-dimethyl-2-cyclohexenone azine by heating in inert solvents in the presence of a catalyst containing a noble metal of the 8th auxiliary group of the Periodic Table of Elements gives high yields when the solvent is an aliphatic ether, especially a lower dialkyl ether of a polyethyleneglycol.

10 Claims, No Drawings

PROCESS FOR THE PREPARATION OF 3,5-DIMETHYLANILINE

From J. Amer. Chem. Soc. 69 (1947), 1907–1908 it is known that 3,5-dimethyl-2-cyclohexen-1-one azine can be converted to 3,5-dimethylaniline by heating in an inert solvent in the presence of a palladium/carbon catalyst. It is indicated in this paper that in numerous tests the optimal conditions for aromatization of the azine have been elaborated, in which tests it has been found out that triethylbenzene was the best solvent. The dimethylaniline was thus obtained with a 50% yield, while other alkylbenzenes gave lower yields, such as the diphenyl ether which brought about a maximum yield of 44%.

Surprisingly, it has not been found that considerably increased yields are obtained in this reaction when the solvent is an aliphatic ether.

The invention provides therefore a process for the preparation of 3,5-dimethylaniline from 3,5-dimethyl-2-cyclohexen-one azine by heating it in an inert solvent in the presence of a catalyst containing a noble metal of the 8th auxiliary group of the Periodic Table of Elements, wherein the solvent is an aliphatic ether.

As compared with other known processes, the preparation of 3,5-dimethylaniline from the azine is distinguished particularly by the fact that the product is obtained in a form free from isomers. It is furthermore advantageous that no aromatic starting materials are required, but that simple aliphatic compounds are used therefor. For example, 3,5-dimethyl-2-cyclohexenone is easily obtainable from acetoacetic ester and acetaldehyde U.S. Pat. No. 4,220,799, and the azine is then prepared therefrom with hydrazine hydrate in a very good yield.

Preferred embodiments of the invention are described in detail as follows:

Owing to the fact that the process of the invention is a reaction in a heterogeneous system, it is advantageous to care for constant good intermixing, which is ensured by corresponding agitation or in simple manner by vigorous boiling.

The reaction temperature is in the range of from 150° to 350° C., preferably 180° to 260° C., because in this range the reaction proceeds rapidly and generally with high selectivity. Depending on the kind of solvent used, the reaction is carried out under a pressure of from 0.001 to 100, especially 0.01 to 20, bar; advantageously, pressure and temperature are adjusted in such a manner that sufficient liquid phase is present and the intended reaction temperature is maintained.

Suitable solvents are in principle all ethers which contain at least one aliphatic group. Ethers having a boiling point of at least about 80° C. are preferably used, because in the case of lower boiling ethers a relatively high pressure is required in order to attain a sufficiently high reaction temperature at which the reaction is completed within an acceptable period of time.

Suitable are high-boiling dialkyl ethers, for example di-n-butyl ether, alkylaryl ethers such as anisol and phenetol, especially polyethers derived from ethyleneglycol and/or propyleneglycol. Suitable polyethers of this type are in the most simple case lower dialkyl ethers of ethyleneglycol or propyleneglycol; preferably, however, lower dialkyl ethers of polyglycols such as ethylenedi-, -tri- or -tetraglycol, or of higher polyglycols are used, furthermore monoaryl ethers such as addition products of ethylene oxide to alkylphenols such as nonylphenol or tributylphenol, the free hydroxy group of which is etherified with lower alkanols. Suitable ethers are furthermore higher polyglycols having free terminal hydroxy groups; preferred, however, are their lower dialkyl ethers having up to 6 carbon atoms in the ether groups, especially the methyl or ethyl ethers.

Advantageously, an ether is chosen the boiling point of which under atmospheric pressure is in the preferred temperature range of from 180° to 260° C., because this solvent allows operations without pressure, and the dehydrogenation proceeds under reflux conditions in an especially rapid and selective manner. Depending on the reaction conditions, the boiling point of the solvent can be chosen in such a manner that on work-up the 3,5-dimethylaniline is in the distillation sump or in the distillate. An advantageous embodiment of the invention is the following: a high-boiling ether is used and the amine is distilled off to that extent to which it is formed, optionally under reduced pressure, so that merely a small amount of solvent is required. When an ether having a lower boiling point than 3,5-dimethylaniline is used, the solvent can be distilled off continuously and recycled to the process in order to save solvent, while the amine is discharged from the sump. These processes can be carried out in a fully continuous manner, too. For example, a solution of the azine in the same solvent which is used for suspending the catalyst, or the molten azine is continuously introduced into the dehydrogenation reactor via a preheater, while simultaneously a corresponding amount of reaction mixture containing the amine formed is discharged. The catalyst is maintained in the reactor for example by means of a frit, or recycled to the reactor after separation, for example by means of a decanter. After separation by distillation from the amine formed, the solvent is reused for dissolving fresh azine.

Alternatively, the azine can be added in a form dissolved in a low-boiling solvent which is continuously distilled off during the dehydrogenation. As such low-boiling solvent for the azine not only ethers, but also other sufficiently inert solvents may be used, for example lower alkanols such as isopropanol.

In addition to the kind of solvent, its amount, too, has a certain influence on the reaction, since the yield decreases with increasing concentration of the azine used and the amine formed. In principle, the yields are the higher the lower the concentration is. For economic reasons, an azine and amine concentration in the reaction mixture of up to about 30 weight %, preferably up to about 15%, relative to the weight of the solvent, is chosen.

In order to keep the azine concentration as low as possible, the speed of the azine addition is advantageously adjusted to the dehydration capacity of the catalyst used, which can be easily determined by a simple preliminary test.

When commercial carrier catalysts are employed, where the noble metal is applied to an inert carrier having a large surface, a catalyst particle size of from about 0.01 to 5, preferably 0.05 to 1, mm is chosen. Depending on the solvent and the catalyst, the reaction suspension can contain from 0.1 to 40% of carrier catalyst, relative to the weight of the liquid reaction medium. Preferred are from 1 to 30%, relative to the weight of the solvent.

The catalyst activity decreases slowly in the course of the reaction, and by-products (di- and triarylamines, carbazoles) are formed to a corresponding extent. These by-products remain in the residue on separation by distillation of the amine. For separation from the solvent, the distillation residue whih has been suction-filtered from the catalyst can be poured onto water, so that the undissolved secondary and tertiary amines are eliminated and the aqueous filtrate clarified with carbon is dehydrated by distillation.

The following examples illustrate the invention; percentages being by weight unless otherwise stated.

EXAMPLE 1

12.5 g of 3,5-dimethyl-2-cyclohexenone azine, 98% strength (corresponding to 12.2 g. of 100% product=0.05 mol) are dissolved in 100 ml of isopropanol. This solution is added dropwise within 3 hours to a boiling suspension (b.p. 215° C.) of 10 g of a palladium carrier catalyst (UM 45 of Messers. Universal-Matthey Products) in 100 g of methylbutyl-diglycol. 100 ml of isopropanol distil off via a small Raschig column. When the azine solution is completely added, stirring is continued for a further 15 minutes at boiling temperature, the batch is cooled to room temperature, and suction-filtered from the catalyst. 88 g of solution are obtained. According to gas chromatography analysis, 12.7% of 3,5-dimethylaniline corresponding to 11.2 g (=0.0924 mol) or 92.4% of theory are contained in this solution.

EXAMPLE 2

Reaction is as in Example 1; however, the isopropanolic azine solution is added dropwise within 6 hours.

92 g of solution containing 12.5% corresponding to 11.5 g of 3,5-dimethylaniline (=0.095 mol) or 95% of theory are obtained.

EXAMPLE 3

The dimethyl ether of a polyethyleneglycol having an average molecular weight of 200 (boiling range 240°–350° C.) is fractionated at 0.4 mbar up to b.p. 225° C. via a column. The distillation residue is clarified with carbon. 10 g of palladium carrier catalyst (UM 45) are added to 150 g of this residue, the batch is heated under reduced pressure of about 26 mbar to about 210° C., and molten, crude 3,5-dimethyl-2-cyclohexenone azine (98% purity, m.p. 71°–79° C.) is added dropwise at a rate of about 1 g per minute and with thorough stirring. 3,5-dimethylaniline is formed which together with some decomposed polyethyleneglycol-dimethyl ether distils over. After about 8 hours, 500 g of 3,5-dimethyl-2-cyclohexenone azine are added dropwise. After addition of the fiirst 250 g of azine (=1.0 mol), 249 g of distillate containing 92%, that is, 229 g, of 3,5-dimethylaniline (=1.89 mols), corresponding to 94.6% of theory, are obtained.

After having added the second half of azine, 236 g of distillate containing 89.6% amine, which corresponds to 211 g of 3,5-dimethylaniline (=1.75 mols) or 87% of theory, are obtained.

The total yield is 440 g of 3,5-dimethylaniline, that is, 90.9% of theory.

EXAMPLE 4

50 g of a 2.8% $Pd/Al_2O_3$ catalyst in powder form and 1 l of dimethyldiethyleneglycol are introduced into a 1.5 liter stainless steel reactor, provided with stirrer, reflux condenser and automatic control of level and pressure. The batch is heated with nitrogen flushing. The automatic pressure control is adjusted to 1.6 bar, so that a reflux temperature of 190° C. results. 100 g per hour of 3,5-dimethyl-2-cyclohexenone azine, dissolved in 900 g of dimethyl-diethyleneglycol, are pumped in, and simultaneously, 1,000 g of reaction product are removed from the reactor via a filter device which keeps the catalyst in the reactor. The hydrogen which forms is discharged via the aromatic pressure control when the pressure in the reactor exceeds 1.6 bar.

Gas chromatography analysis of the reaction product gives 8.9% of 3,5-dimethylaniline. After having distilled off the dimethyl-diethyleneglycol, 99.6% 3,5-dimethylaniline distils over at 93° C./12 mbar.

What is claimed is:

1. A process for the preparation of 3,5-dimethylaniline from 3,5-dimethyl-2-cyclohexen-one azine by heating it in an inert solvent in the presence of a catalyst containing a noble metal of the 8th auxiliary group of the Perioc Table of Elements, wherein the solvent is an aliphatic ether.

2. A process as claimed in claim 1, wherein the ether is a lower dialkyl ether of a polyethyleneglycol.

3. A process as claimed in claim 1, wherein the concentration of the azine in the reaction mixture does not exceed 30 weight %.

4. A process as claimed in claim 1, wherein the concentration of the azine does not exceed 15 weight %, relative to the solvent.

5. A process as claimed in claim 1, wherein the azine is added to the heated solvent.

6. A process as claimed in claim 1, wherein the temperature is 150° to 350° C.

7. A process as claimed in claim 1, wherein the temperature is 180° to 260° C.

8. A process as claimed in claim 1, wherein the pressure is 0.001 to 100 bar.

9. A process as claimed in claim 1, wherein the pressure is 0.01 to 20 bar.

10. A process as claimed in claim 1, wherein the ether has a boiling point of 180° to 260° C.

* * * * *